(12) United States Patent
Carey et al.

(10) Patent No.: US 6,197,997 B1
(45) Date of Patent: Mar. 6, 2001

(54) LOADED ION EXCHANGE RESINS, THEIR PREPARATION AND USES

(75) Inventors: John Laurence Carey, East Yorkshire; Michael David Jones; Andrew David Poole, both of Yorkshire, all of (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/112,513

(22) Filed: Jul. 9, 1998

(30) Foreign Application Priority Data

Jul. 23, 1997 (GB) .................................................. 9715489

(51) Int. Cl.⁷ .................................................. C07C 51/10
(52) U.S. Cl. .................................................. 562/406
(58) Field of Search .................................................. 562/406

(56) References Cited

U.S. PATENT DOCUMENTS 5,416,237 * 5/1995 Aubigne et al. ...................... 560/519

FOREIGN PATENT DOCUMENTS 0 196 173 10/1986 (EP) .
0 296 584 12/1988 (EP) .

OTHER PUBLICATIONS

Japanese Abstract of JP–09291058, Hiroyuki et al, "Method of Moving Iodine Compounds Contained . . . " (1997).

* cited by examiner

Primary Examiner—Joseph K. McKane
Assistant Examiner—Joseph Murray
(74) Attorney, Agent, or Firm—Nixon & Vanderhye

(57) ABSTRACT

A loaded ion-exchange resin, which resin has been loaded in its shrunken form. Also a process for removing iodide compounds from a liquid carboxylic acid and/or carboxylic acid anhydride obtained from the Group VIII noble metal catalysed, alkyl iodide co-catalysed carbonylation of alcohols and/or their reactive derivatives which process comprises contacting the liquid carboxylic acid and/or carboxylic acid anhydride with a metal loaded ion-exchange resin as described above wherein the metal is one or more of the metals silver, palladium or mercury.

6 Claims, No Drawings

LOADED ION EXCHANGE RESINS, THEIR PREPARATION AND USES

The present invention relates in general to loaded ion-exchange resins, their preparation, their use in aqueous and non-aqueous solvent applications and, in particular, their use in the purification of acetic acid and/or acetic anhydride prepared by the Group VIII noble metal catalysed, methyl iodide promoted carbonylation of methanol and/or methyl acetate by removal therefrom of iodide derivatives, eg. alkyl iodides and the like.

Ion-exchange resins are well-known commercial products. Typically, they are synthetic insoluble cross-linked polymers carrying acidic or basic side-groups which have high exchange capacity. They have many applications, including water-treatment, extraction, separation, analysis and catalysis. A feature of ion-exchange resins is that to a greater or lesser extent their volume can change with changes in their solvent environment, for example from aqueous to organic and vice-versa. Thus, for example, the ion-exchange gel resin, AMBERLITE IR120™ can shrink by as much as 40% when its environment is changed from aqueous (as purchased) to the silver-exchanged form in acetic acid and can swell correspondingly in the reverse operation. Macroreticular resins too can shrink, albeit less markedly, when their environment is changed from aqueous to non-aqueous. For many of the applications referred to hereinbefore ion-exchange resins are used in loaded form, for example loaded with metals, generally by ion-exchange or impregnation of the swollen resin. It is our experience that when ion-exchange gel resins at least are loaded in the swollen form, their effectiveness in the shrunken form is not that which might be expected from the amount of the loaded moiety present.

The problem to be solved by the present invention is that of providing a loaded ion-exchange resin having improved effectiveness in the shrunken form. We have surprisingly found that a solution to the problem is to load the ion-exchange resin in the shrunken form, as opposed to the swollen form.

Accordingly the present invention provides a loaded ion-exchange resin, which resin has been loaded in its shrunken form.

The ion-exchange resin may be any suitable resin. It may be, for example, an ion-exchange gel resin, a macroreticular ion-exchange resin or indeed any other resin which experiences a volume change upon changing the nature of its solvent environment. The invention is particularly applicable to gel resins because these exhibit a pronounced loss in effectiveness upon changing their environment from aqueous to organic.

The ion-exchange resin may be loaded with $H^+$ ions, at least one metal and/or a group of atoms which together form a charged moiety. The metal may be in the form of a cation of the metal. The metal may be any metal of Groups I to VIII of the Periodic Table, for example a metal of Groups Ib, IIb, III, Va, VIa, VIIa and VIII. The Periodic Table referred to herein is that to be found in Advanced Inorganic Chemistry by Cotton and Wilkinson, Fourth Edition, published in 1980 by John Wiley and Sons. Preferred metals include silver, palladium and mercury. Alternatively, or in addition, the ion-exchange resin may be loaded with a group of atoms which together form a charged moiety. The charged moiety may be anionic or cationic. A typical anionic charged moiety may be a sulphonic acid anion.

It is believed though we do not wish to be bound by any theory that ion-exchange resins loaded in the swollen form may lose their effectiveness in the shrunken form because a high proportion of the loaded moiety becomes trapped within the resin during its collapse consequent upon change of solvent and hence is unavailable for the purpose for which it was loaded.

In another embodiment the present invention provides a process for the production of a loaded ion-exchange resin as hereinbefore described which process comprises loading an ion-exchange resin in its shrunken form.

Suitable ion-exchange resins and loading moieties are as hereinbefore described.

The shrunken form of the resin may suitably be obtained by changing the liquid environment of the resin from a swelling environment to a shrinking environment. Thus, for example, removal of water from a gel resin and replacement with acetic acid provides the resin in its shrunken form. In a preferred mode of operating the process the shrunken form of the resin is thereafter loaded. Loading of the resin in its shrunken form may suitably be accomplished by ion-exchange and/or by impregnation. Loading may be accomplished at ambient or elevated temperature.

The loaded ion-exchange resins of the present invention may be used in any process in which a resin is conventionally employed, particularly in those processes in which the solvent environment would otherwise cause shrinkage of the gel with associated loss in effectiveness.

In another aspect the present invention therefore provides for use of a loaded ion-exchange resin as hereinbefore described in a process in which the solvent environment causes shrinkage of the resin.

Such a process is the removal of iodide compounds from the liquid carboxylic acids and/or carboxylic anhydrides obtained from the Group VIII noble metal catalysed, alkyl iodide co-catalysed carbonylation of alcohols and/or their reactive derivatives. It is known that a problem associated with acetic acid and/or acetic anhydride so-produced is that even after distillation the acetic acid and/or acetic anhydride frequently contains small amounts of iodide impurities. Whilst the exact nature of these compounds is not known for certain, they probably comprise a mixture of methyl iodide and other higher alkyl iodides, HI and iodide salts. Such impurities are particularly troublesome since they can poison many of the catalysts which are employed in subsequent chemical conversions of the acetic acid and/or acetic anhydride. A case in point is the catalysts used to prepare vinyl acetate from ethylene and acetic acid which are extremely sensitive to iodide impurities.

Accordingly in a further embodiment the present invention provides a process for removing iodide compounds from a liquid carboxylic acid and/or carboxylic anhydride obtained from the Group VIII noble metal catalysed, alkyl iodide co-catalysed carbonylation of alcohols and/or their reactive derivatives which process comprises contacting the liquid carboxylic acid and/or carboxylic acid anhydride with a metal loaded ion-exchange resin as hereinbefore described wherein the metal is one or more of the metals silver, palladium or mercury.

Processes for producing a liquid carboxylic acid and/or anhydride by the Group VIII noble metal catalysed, alkyl iodide co-catalysed carbonylation of alcohols and/or their reactive derivatives are well-known in the art.

In a preferred aspect this embodiment provides a process for removing iodide compounds from acetic acid and/or acetic anhydride obtained from the rhodium-catalysed, methyl iodide co-catalysed carbonylation of methanol and/or methyl acetate.

A preferred ion-exchange resin is an ion-exchange gel resin, for example AMBERLITE IR120, and AMBERLITE IR118. The ion-exchange resin is preferably one which is loaded with silver.

The iodide compounds may be $C_1$ to $C_{10}$ alkyl iodides, hydrogen iodide or iodide salts, and in particular methyl iodide and/or $C_5$ to $C_7$ iodides.

The process may suitably be carried out by passing liquid acetic acid and/or acetic anhydride contaminated with iodide compounds through a fixed bed of the resin at a predetermined rate. Preferably the resin bed is graded by backflushing before use. The feed rate employed will depend on a number of variables including the amount of iodide impurities in the acetic acid and/or acetic anhydride, the degree of acetic acid and/or acetic anhydride purity required and the particular resin employed. Typical flow rates are in the range 0.5 to 50, preferably 5 to 15 bed volumes per hour. Optimum flow rates will depend upon the temperature of the resin bed and can readily be determined.

The temperature at which the process is carried out must be high enough to prevent acetic acid and/or acetic anhydride from freezing at one extreme or boiling at the other. Typical ranges are from 20 to 120° C., preferably from 25 to 115° C. Whilst in general it is desirable to operate at as high a temperature as possible, in order to effect maximum iodides removal, it may, in certain circumstances for reasons of economy be desirable to operate at a lower temperature and modify one or other of the process variables to reach the target level of iodide removal. The thermal stability of the resin may also impose an upper limit on the operating temperature.

Typically, a silver loaded ion-exchange resin for use in the process as hereinbefore described may be prepared by slurrying an ion-exchange gel resin with silver oxide in acetic acid. Shrinkage of the gel resin may be accomplished during the slurrying step alone or by a preliminary step in which, for example, the swollen resin is treated with acetic acid in the absence of silver oxide.

We have found that an advantage of using a silver-loaded ion-exchange gel resin according to the invention in the continuous operation of the iodide removal process as hereinbefore described is that the iodide removal lifetime of the resin can be greater than twice that of the resin loaded in an aqueous medium in which the resin is swollen and that this advantage is achievable using half the amount of silver oxide for loading the resin.

The invention will now be illustrated by reference to the following Examples.

A—Loading of the gel resin with silver

EXAMPLE 1—in Acetic Acid (i) 100 mL of the water wet proton form of AMBERLITE IR120 resin was weighed out and subsequently placed in a conical flask containing 100 mL of acetic acid and allowed to stir at room temperature for 3 minutes.

(ii) The resin was then filtered and a further 100 mL of acetic acid added and allowed to stir at room temperature for 3 minutes.

(iii) Step (ii) was repeated once more before putting the resin in acetic acid (100 mL) and allowing it to stir at room temperature for 1 hour.

(iv) Step (ii) was repeated three more times.

(v) The resin was then placed in a conical flask with 180 mL of acetic acid and warmed to 50° C. Silver (I) oxide (3.8 g) was added slowly to the resin slurry over a period of 30 minutes and the resin was then allowed to stir for a further 90 minutes at 50° C.

(vi) The flask and contents were allowed to cool to room temperature and thereafter the loaded resin was filtered from solution and washed three times as described in step (ii).

(vii) The loaded resin obtained from (vi) was then stored in acetic acid solution prior to use in a resin bed.

After drying to constant mass, the resin was found to contain 7.4% w/w silver.

Comparison Test 1—in Water/Acetic Acid Mixture (i) 100 mL of the water wet proton form of AMBERLITE IR120 resin was weighed out and subsequently placed in a conical flask containing 100 mL of de-ionised water and allowed to stir at room temperature for 3 minutes.

(ii) The resin was then filtered and a further 100 mL of de-ionised water added and allowed to stir at room temperature for 3 minutes.

(iii) Step (ii) was repeated.

(iv) The resin was then placed in a conical flask with 80 mL of de-ionised water. Silver (I) oxide (7.6 g) was added to the resin, and was then allowed to stir for 5 minutes at room temperature.

(v) Acetic acid (100 mL) was added to the resin mixture and heated to 50° C. with stirring for 90 minutes.

(vi) The flask and contents were allowed to cool to room temperature and thereafter the loaded resin was filtered from solution and washed three times as described in step (ii).

(vii) The loaded resin obtained from (v) was then washed thoroughly with acetic acid prior to use in a resin bed.

After drying to constant mass the resin was found to contain 12.7% w/w silver.

This is not an example according to the present invention because the resin was loaded with silver in the swollen form.

B—Removal of iodides

Comparison Test 2

Using a standard screening programme 50 mL of the resin prepared in Comparison Test 1, was loaded into a resin bed, acetic acid dosed with 200 ppb hexyl iodide was fed over the bed at an LHSV of 10 at an operating temperature of 100° C.

After 94 hours of operation, the product acid contained 37 ppb hexyl iodide.

EXAMPLE 2

The procedure described in Comparison Test 2 was repeated except that the resin prepared in Example 1 was employed in the screening programme.

The iodide removal ability of this resin was found to be significantly better than that described in Comparison Test 2. After 288 hours, the product acid contained no more than 2 ppb hexyl iodide. Only after 560.5 hours of operation did the product acid contain greater than 37 ppb hexyl iodide.

This example shows that shrunken AMBERLITE IR120 resin silver-loaded in acetic acid solution has superior iodide removal abilities to one prepared in an acetic acid/water mixture.

Comparison Test 3

Comparison Test 1 was repeated except that the resin AMBERLITE IR118 was used instead of IR120, and was loaded with 20.9% w/w Ag. The resulting Ag loaded resin was tested for hexyl iodide removal using a feed containing 20 ppm hexyl iodide. After 3 hours the hexyl iodide level was reduced from 20 ppm to 729 ppb.

EXAMPLE 3

The silver loading procedure described in Example 1 was repeated except that the resin AMBERLITE IR118 was used instead of IR 120, and was loaded with 7.0% w/w Ag. The resulting Ag loaded resin was tested for hexyl iodide removal using a 20 ppm hexyl iodide feed. After 141 hours the hexyl iodide level was reduced from 20 ppm to 497 ppb.

This example shows that shrunken AMBERLITE IR118 resin silver-loaded in acetic acid solution has superior iodide removal abilities to one prepared in an acetic acid/water mixture.

We claim:

1. A process for removing iodide compounds from a liquid carboxylic acid and/or carboxylic acid anhydride obtained from the Group VIII noble metal catalysed, alkyl iodide co-catalysed carbonylation of alcohols and/or their reactive derivatives which process comprises contacting the liquid carboxylic acid and/or carboxylic acid anhydride with a metal loaded ion-exchange resin which resin has been loaded in its shrunken form, wherein the metal is one or more of the metals silver, palladium or mercury.

2. A process according to claim 1 wherein the ion-exchange resin is a gel resin.

3. A process according to claim 1 wherein the resin is loaded with silver.

4. A process according to claim 1 wherein the iodide compounds comprise $C_1$ to $C_{10}$ alkyl iodides, hydrogen iodide and/or iodide salts.

5. A process according to claim 4 wherein the iodide compounds comprise methyl iodide and/or $C_5$ to $C_7$ iodides.

6. A process according to claim 1 wherein iodide compounds are removed from acetic acid and/or acetic anhydride obtained from the rhodium-catalysed, methyl iodide co-catalysed carbonylation of methanol and/or methyl acetate.

* * * * *